United States Patent
Lipshaw et al.

(10) Patent No.: US 9,642,766 B2
(45) Date of Patent: *May 9, 2017

(54) GRADUATED COMPRESSION DEVICE HAVING SEPARATE BODY AND BANDS

(71) Applicant: MEDI MANUFACTURING, INC., Whitsett, NC (US)

(72) Inventors: Moses A. Lipshaw, Encinitas, CA (US); Thomas Richardson, Del Mar, CA (US); Teresa Kennerknecht, San Diego, CA (US); Sandra Anne Shaw, Coronado, CA (US)

(73) Assignee: MEDI MANFACTURING, INC., Whitsett, NC (US)

( * ) Notice: Subject to any disclaimer, the term of this patent is extended or adjusted under 35 U.S.C. 154(b) by 347 days.

This patent is subject to a terminal disclaimer.

(21) Appl. No.: 14/447,542

(22) Filed: Jul. 30, 2014

(65) Prior Publication Data

US 2016/0030267 A1    Feb. 4, 2016
US 2016/0166458 A9    Jun. 16, 2016

Related U.S. Application Data

(63) Continuation of application No. 13/346,689, filed on Jan. 9, 2012, now Pat. No. 8,801,645.

(60) Provisional application No. 61/431,371, filed on Jan. 10, 2011.

(51) Int. Cl.
 *A61H 1/00* (2006.01)
(52) U.S. Cl.
 CPC ................................. *A61H 1/008* (2013.01)
(58) Field of Classification Search
 CPC ....................................................... A61H 1/008

USPC .......... 450/94, 100, 101; 602/41, 60, 75–77; 2/44

See application file for complete search history.

(56) References Cited

U.S. PATENT DOCUMENTS

| | | |
|---|---|---|
| 2,280,025 A | 4/1942 | Bollinger |
| 3,538,914 A | 11/1970 | Meyers |
| 3,856,008 A | 12/1974 | Fowler et al. |
| 4,215,687 A | 8/1980 | Shaw |
| 4,297,997 A | 11/1981 | Clayton |
| D278,083 S | 3/1985 | Meier |
| 4,590,932 A | 5/1986 | Wilkerson |
| 5,108,455 A | 4/1992 | Telikicherla et al. |
| 5,120,300 A | 6/1992 | Shaw |

(Continued)

FOREIGN PATENT DOCUMENTS

JP    3120206 U    3/2006

OTHER PUBLICATIONS

PCT International Search Report in related PCT Application No. PCT/US12/20765, mailed May 4, 2012.

(Continued)

*Primary Examiner* — Tarla Patel
(74) *Attorney, Agent, or Firm* — Troutman Sanders LLP

(57) ABSTRACT

A compression garment, having: (a) a body portion dimensioned to be wrapped around a body limb, the body portion having a top edge, a bottom edge and a pair of opposite side edges; and (b) a plurality of bands, wherein the bands are each attachable onto the body portion at a plurality of different locations, and wherein the bands wrap around part of the body portion when the body portion is wrapped around the body limb to apply compression force to the body limb.

20 Claims, 25 Drawing Sheets

(56) References Cited

U.S. PATENT DOCUMENTS

| | | |
|---|---|---|
| 5,254,122 A | 10/1993 | Shaw |
| 5,425,702 A | 6/1995 | Carn et al. |
| 5,472,414 A | 12/1995 | Detty |
| 5,520,630 A | 5/1996 | Daneshvar |
| 5,653,244 A | 8/1997 | Shaw |
| 5,897,518 A | 4/1999 | Shaw |
| 5,906,206 A | 5/1999 | Shaw et al. |
| 5,918,602 A | 7/1999 | Shaw et al. |
| 5,993,405 A | 11/1999 | Wynn |
| 6,053,169 A | 4/2000 | Hunt et al. |
| 6,109,267 A | 8/2000 | Shaw et al. |
| 6,190,344 B1 | 2/2001 | Bobroff |
| 6,338,723 B1 | 1/2002 | Carpenter et al. |
| 7,135,007 B2 | 11/2006 | Scott et al. |
| 7,258,676 B2 | 8/2007 | Calderon et al. |
| 7,329,232 B2 | 2/2008 | Lipshaw et al. |
| 7,867,185 B2 | 1/2011 | Lipshaw |
| 7,942,838 B2 | 5/2011 | Farrow |
| 8,801,645 B2 * | 8/2014 | Lipshaw .............. A61F 13/085 450/101 |
| 2003/0171706 A1 | 9/2003 | Nelson |
| 2005/0143683 A1 | 6/2005 | Waldridge et al. |
| 2005/0192524 A1 | 9/2005 | Lipshaw et al. |
| 2005/0209545 A1 | 9/2005 | Farrow et al. |
| 2005/0288614 A1 | 12/2005 | Weatherly |
| 2007/0179421 A1 | 8/2007 | Farrow |
| 2007/0282232 A1 | 12/2007 | Hoffman |
| 2008/0086071 A1 | 4/2008 | Weatherly |
| 2009/0247921 A1 | 10/2009 | Weitzen |
| 2010/0004563 A1 | 1/2010 | Lipshaw |
| 2010/0056973 A1 | 3/2010 | Farrow et al. |
| 2010/0312160 A1 | 12/2010 | Creighton et al. |
| 2011/0257575 A1 | 10/2011 | Farrow et al. |

OTHER PUBLICATIONS

Supplemental European Search Report in Related European Application No. EP10833827, mailed Aug. 28, 2012.

* cited by examiner

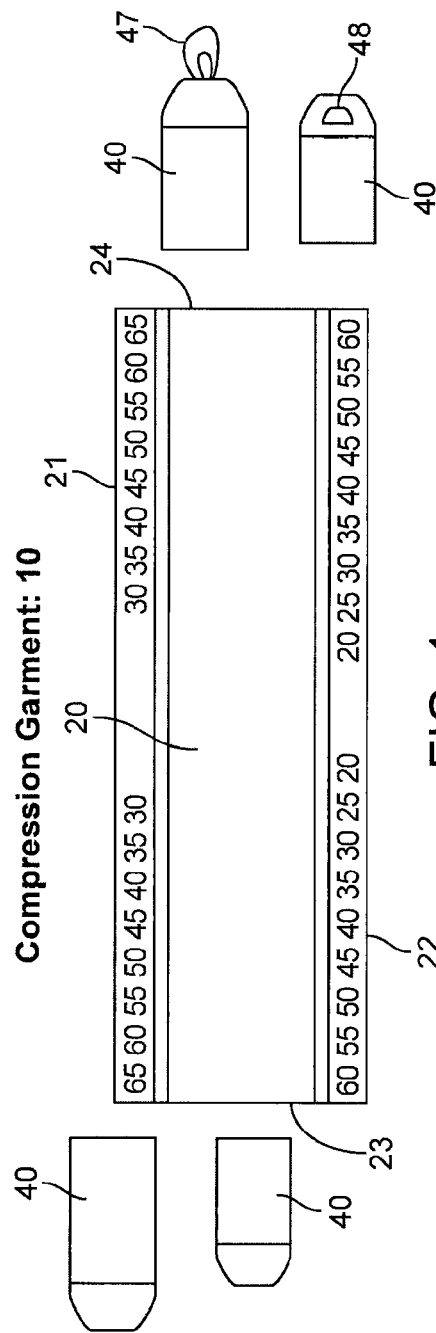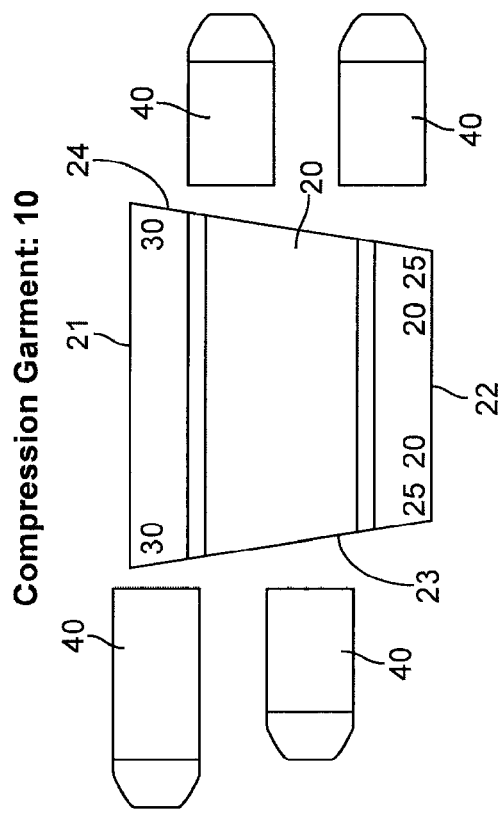

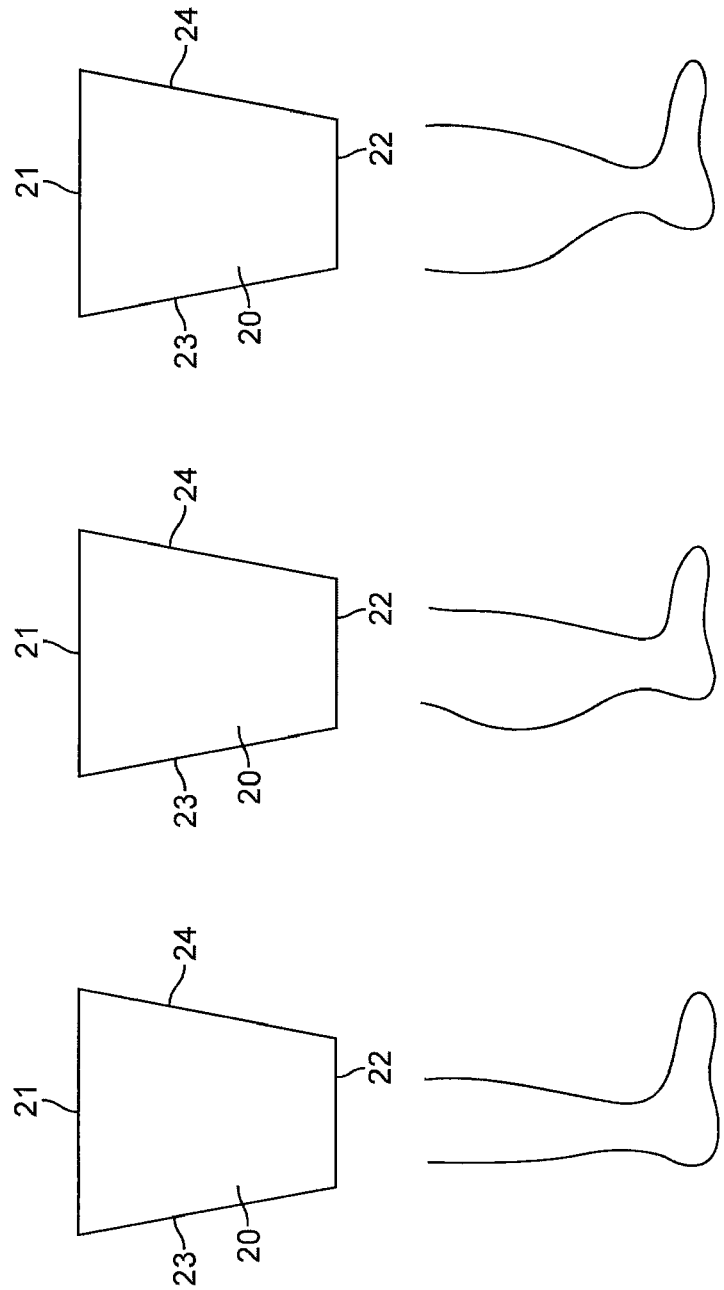

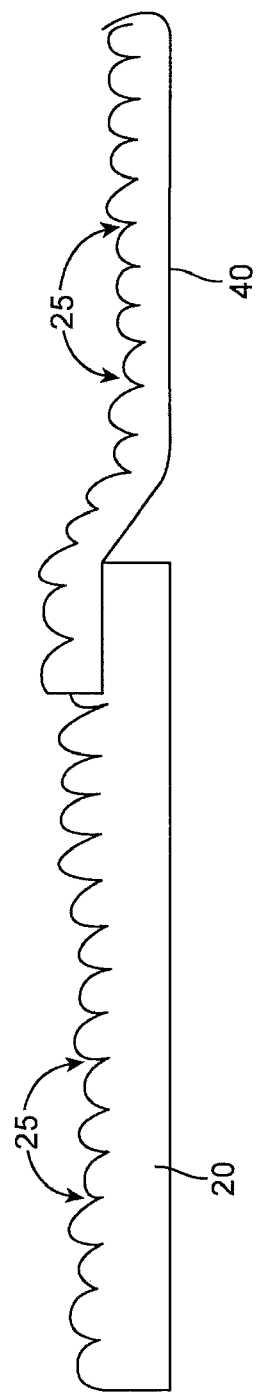

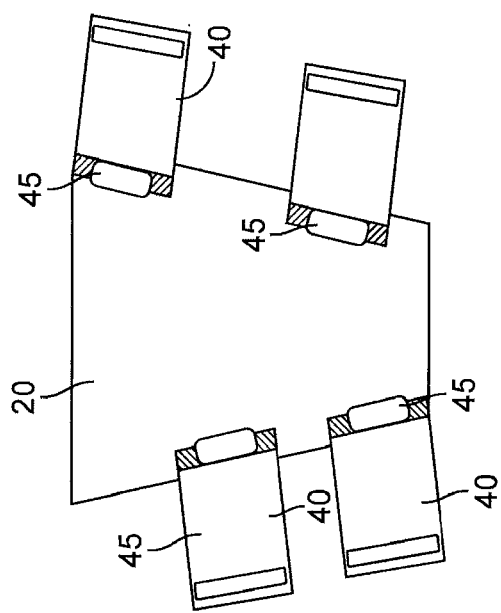
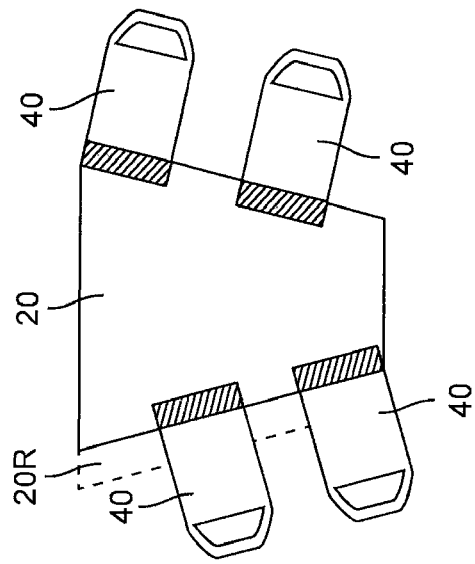
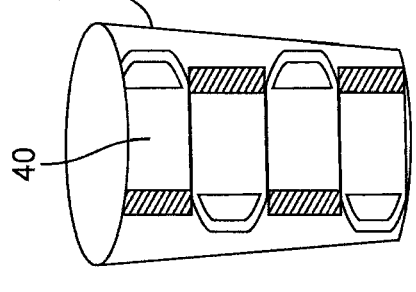
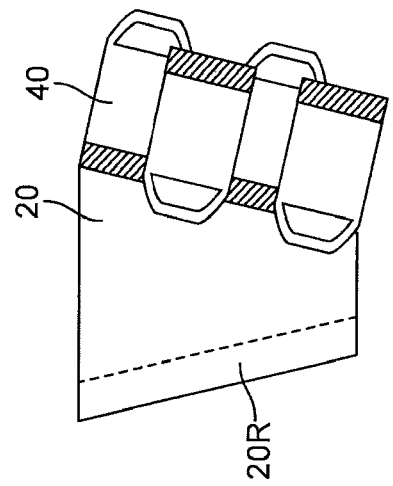
FIG. 13
FIG. 14A
FIG. 14B
FIG. 14C

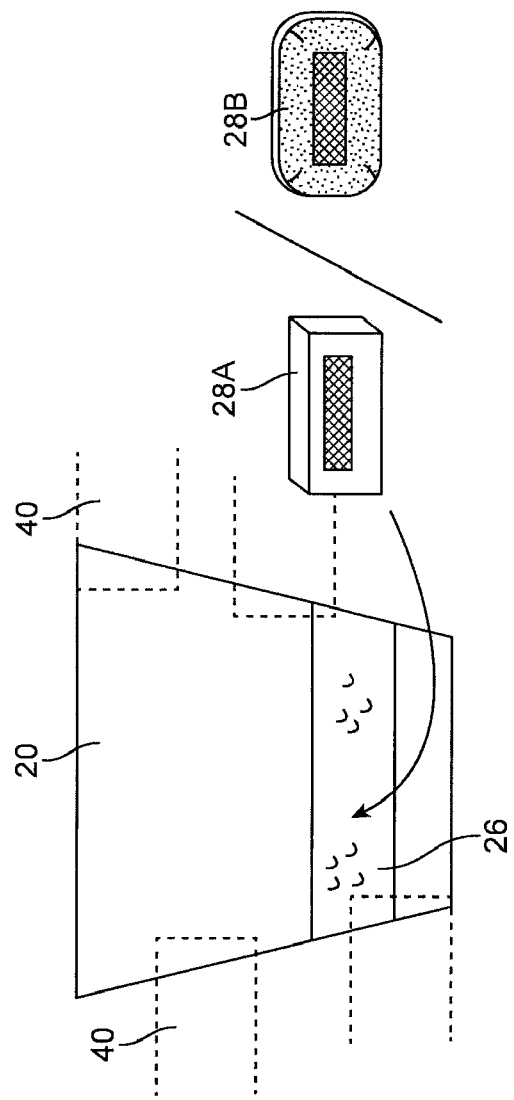

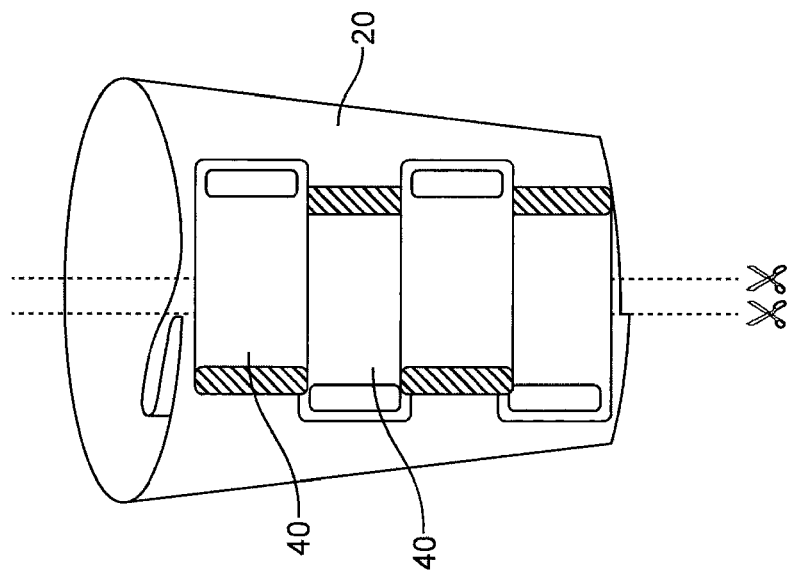
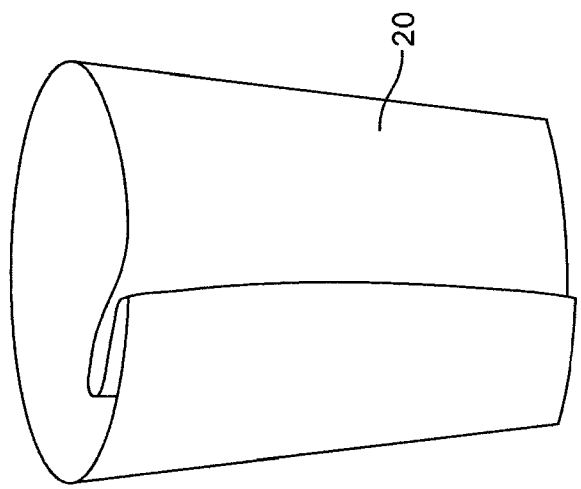
FIG. 17B
FIG. 17A

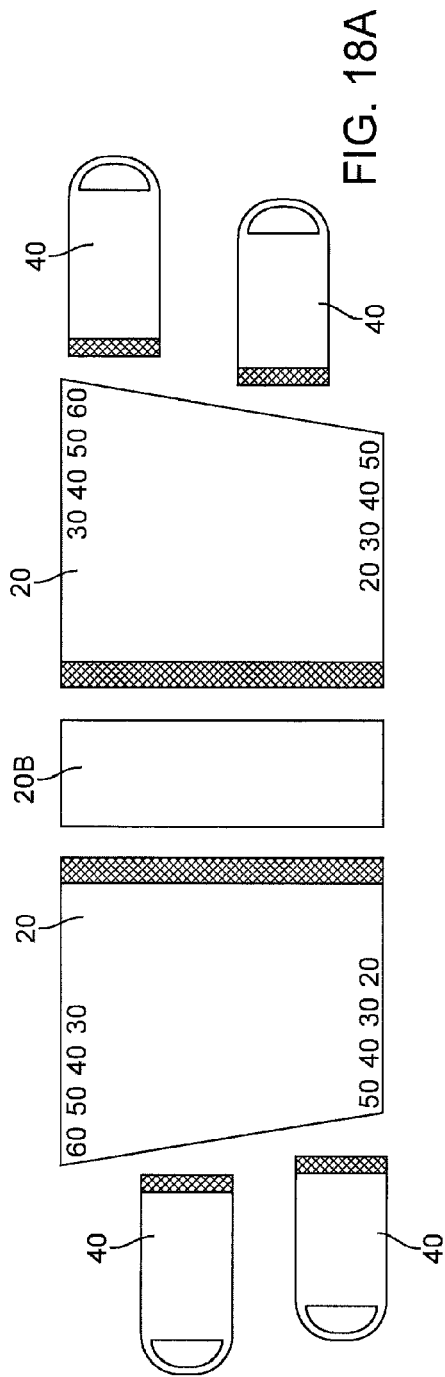

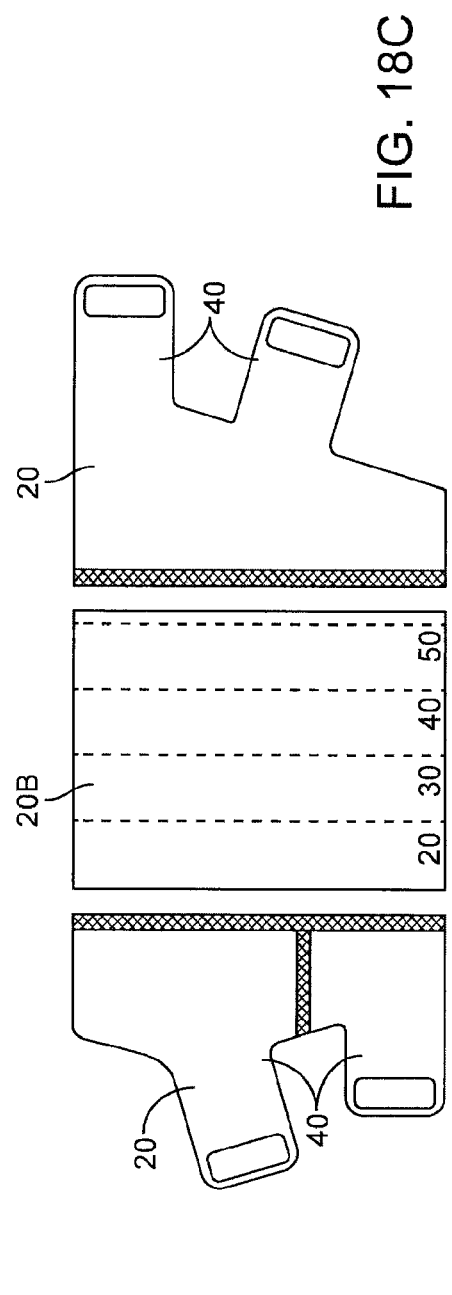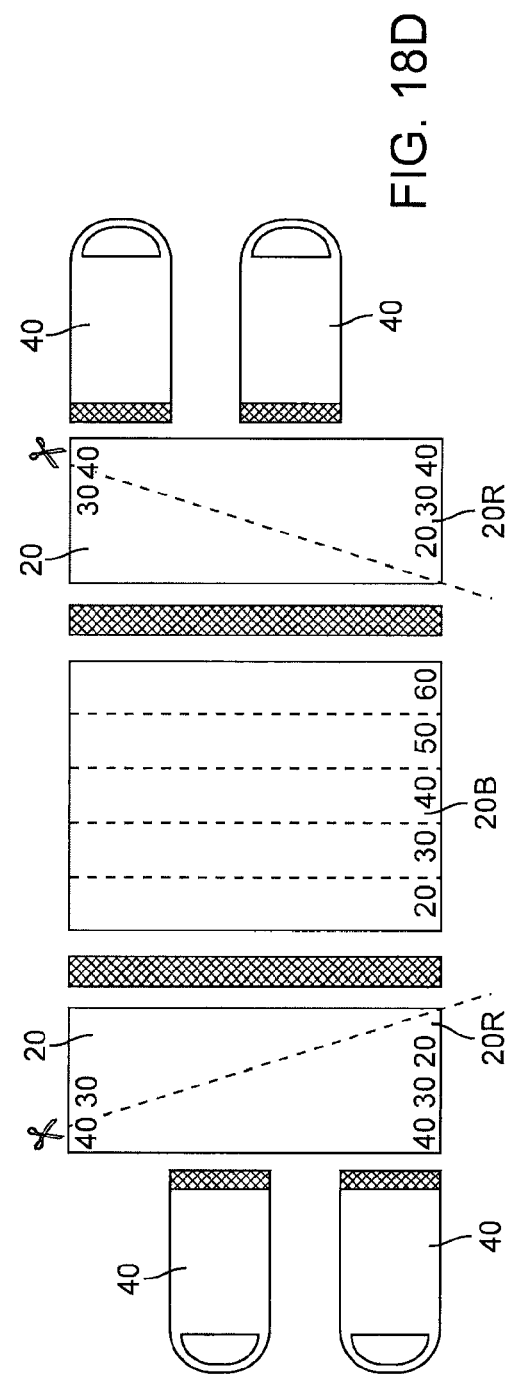

GRADUATED COMPRESSION DEVICE HAVING SEPARATE BODY AND BANDS

RELATED APPLICATION

The present invention claims priority to U.S. Provisional Patent Application 61/431,371; filed Jan. 10, 2011 entitled "Graduated Compression Device For The Treatment Of Circulatory Disorders Such As Lymphedema And Venous Diseases", the full disclosure of which is incorporated herein by reference in its entirety.

TECHNICAL FIELD

The present invention relates to devices that treat circulatory disorders such as lymphedema, edema and venous diseases.

BACKGROUND OF THE INVENTION

A common treatment for circulatory disorders such as lymphedema, edema and venous diseases is to wear a compression garment. Current compression garments are available in various ready-to-wear standard sizes. Unfortunately, a wide array of inventory must be kept on hand when distributing ready-to-wear garments in order to accommodate the population majority. Although compression garments have been designed that can be modified in circumference or length to obtain a better fit, the "nearest" size must still be chosen.

Alternatively, custom made-to-measure garments have also been produced as a form of treatment. Unfortunately, measuring, sizing, and ordering these made-to-measure garments is time consuming and may still not result in a properly fitted compression garment. For limbs that are outside of the standard ready-to-wear size range, custom garments need to be built to match the curvature, length and circumference of the limb. As a result, many measurements are needed to make these custom garments and there is a period between measuring, ordering, production and fitting of the garment where the limb profile may change, which can result in an improper fit due to the time it takes for the patient to receive their garment.

Various compression garments have tried trimming-to-fit methods where longer bands are cut down from the largest size to fit the patient. Unfortunately, these bands need to be trimmed separately or in pairs and angled in a manner that best conforms to the shape of the limb. This is a slow and time consuming process. Working out the correct lengths and angles of each band can be very difficult, and is often made more difficult due to the fact that the bands need to overlap to obtain complete coverage.

Other compression modalities such as bandaging have also been used. An advantage of bandaging is that it can be used on 100% of the population with one inventory set. Unfortunately, bandaging is very time consuming and does not have the benefit of quick and easy application as compared to standard compression garments. In addition, bandaging is not guaranteed to provide reliable/consistent compression levels, and cannot be adjusted as the limb shape and compression needs change.

Furthermore, although "fixed bands" compression garments can be modified in circumference from one direction to fit most users, the garment can still only be modified from one direction and the angle of the bands can not be adjusted. As a result, the garment cannot sufficiently contour to limbs that feature large changes in circumference. For limbs out of the standard ready to wear size range, custom garments can be built to match the curvature of the limb. Unfortunately, many measurements are needed to make these garments and there is a period between production and fitting of the garment where the limb profile may change. This can result in an improper fit and the patient has to wait to receive their garment.

What is instead desired is a one-size-fits-all compression garment that can be easily and quickly tailored to match the patient's limb length and circumference profile.

SUMMARY OF THE INVENTION

The present invention provides a one-size-fits-all compression garment that can easily and quickly be tailored to match the circumference profile and length of a particular patient's body portion. An advantage of the present garment is that it can be provided in one size for all patients (since the actual sizing and adjustment of the garment can be done by the therapist or end user or clinician). Another advantage of the present garment is that it is simple to put on and very easy for therapist or a clinician or end user to shape, size correctly, and adjust accordingly.

In a preferred embodiment, the present invention comprises a therapeutic compression garment, having: a body portion dimensioned to be wrapped around a portion of the body, including but not limited to a limb or torso, the body portion preferably being flat and having a top edge, a bottom edge and a pair of opposite side edges; and a plurality of bands, wherein the bands are each attachable onto the flat body portion at a plurality of different locations, and wherein the bands wrap around part of the body portion when the flat body portion is wrapped around the body limb to apply a compression force to the body limb.

In its simplest form, the present invention comprises a body portion that is cut down equally from both sides (and/or top or bottom) to form a preferred shape, and four separate bands that are secured onto this body portion. Preferably, the bands extend from opposite sides and are juxtaposed to wrap part way around the body portion to provide therapeutic compression. The bands may be attached to the flat body portion by hook and loop fasteners, or alternatively by gluing or by zippers, or any other suitable system.

In preferred embodiments, the top edge of the body portion is wider than the bottom edge and the opposite side edges of the body portion taper inwardly from the top to bottom edges. The top edge of the body portion is dimensioned to wrap around the calf, thigh or upper arm and the bottom edge of the body portion is dimensioned to wrap around the ankle, wrist or knee. Specifically, the body limb circumference is first measured at these two locations and the body portion is then cut into a tapered shape from a wide top to a narrow bottom. Preferably, measurement indicia run along the top and bottom edges of the body portion, and the side edges of the body portion are cut down equally such that the measured diameters of the patient's limb matches the measurements running along the top and bottom of the body portion of the garment. Additional indicia can be used to further refine the band placement on the body portion. For example, band placement markers can be used along the height of the garment.

In use, the body portion is wrapped around the body limb and the bands are wrapped around a portion of the body to apply a therapeutic compression force to the limb. In accordance with the present invention, the position of each of the bands can be varied such that they may be mounted at various preferred locations on the flat body portion of the garment. As a result, each band can be angled independently, aiding in achieving a contoured fit around the limb. This feature allows the fitting of the garment to be customized to the particular individual's body dimensions.

Preferably, the body portion has cut away regions for shortening the length of the garment along a body limb, as well as for narrowing the width of the compression garment.

Existing compression garments rely on trimming bands for size adjustments. In contrast, the present invention relies on trimming the body portion of the garment and not the bands. The fitting process is therefore simplified by not having to alter any of the bands. It is to be understood, however, that the present invention also encompasses embodiments in which trimmable bands are provided. Such trimmable bands may be useful when dealing with very small circumference limbs (to avoid the bands wrapping unnecessarily far around the limb). Another advantage of the present garment is that it can be provided in one size for all patients (since the actual sizing and adjustment of the garment can be done by the therapist or end user or clinician). Yet another advantage of the present garment is that it is simple to put on and very easy for a clinician or end user to shape, size correctly, and adjust accordingly.

BRIEF DESCRIPTION OF THE DRAWINGS

FIG. 1 is an illustration of the parts of the compression garment prior to cutting the body portion to fit a particular individual.

FIG. 2 is an illustration of the parts of the compression garment after the body portion has been cut to fit a particular individual.

FIG. 3A is an illustration of the body portion dimensioned for a patient having a small calf and a small ankle.

FIG. 3B is an illustration of the flat body portion dimensioned for a patient having a medium calf and a small ankle.

FIG. 3C is an illustration of the flat body portion dimensioned for a patient having a large calf and a small ankle.

FIG. 12B is a side elevation view corresponding to FIG. 12A showing channels to create alternating regions of high and low pressure.

FIG. 13 is an embodiment in which each of the bands have reinforcement tabs securing them to the body portion.

FIG. 14A is another embodiment with all the bands extending from one side of the garment.

FIG. 14B shows the embodiment of FIG. 14A wrapped together.

FIG. 14 C shows the embodiment of FIGS. 14A and 14B after the fitting is done.

FIG. 15 is an embodiment of the invention showing a strip for attachment of either additional foam pads or wound dressings.

FIG. 17A is a cylindrical piece body that is wrapped onto itself.

FIG. 17B is the embodiment of FIG. 17A showing the bands attached thereto.

FIGS. 18A to 18D show various embodiments of the invention with a bridge portion in the middle of the body portion.

Figure 4:
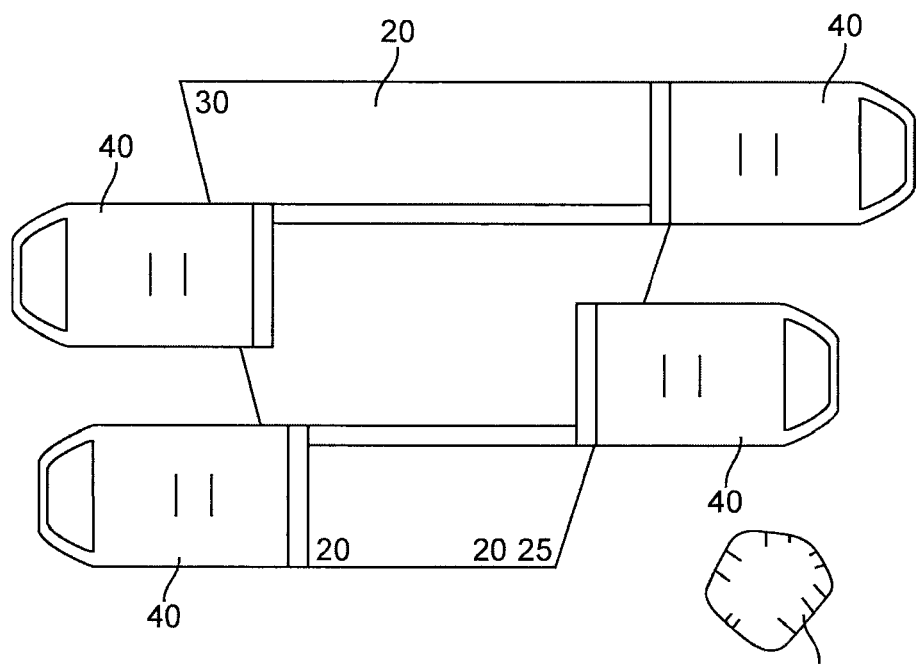
FIG. 4 is an illustration of the bands attached onto the body portion.

DETAILED DESCRIPTION OF THE DRAWINGS:

FIG. 1 shows a compression garment prior to cutting the body portion to fit a particular individual, and FIG. 2 shows the compression garment after the body portion has been cut to fit the patient. The examples described herein typically refer to a limb (i.e.: an arm or leg). However, it is to be understood that the present invention is not limited to application only to limbs. Instead, it may also be used on the body torso, neck, head, fingers, toes, etc.

First, as seen in FIG. 1, a therapeutic compression garment 10 is provided. Garment 10 has a flat body portion 20 that wraps around a body limb. Body portion 20 is preferably made of a breathable short stretch foam laminate material with unbroken loop material, but other suitable, elastic and inelastic woven and non-woven materials can also be used. Moreover, different bands can be made of different materials having different stretch characteristics. For example, bands can be made of decreasing power from the bottom to the top so that if both were wrapped around the limb, the one with more power would apply more compression. Furthermore, since the circumference is known during the fitting process, a band with known power can be chosen such that the compression level beneath the garment is known when the band is applied with just enough tension to completely elongate the material (e.g. 20-30 mmHg, 30-40 mmHg, etc.) In optional embodiments, all or portions of the garment may be made of active textiles (i.e.: that change heat, electricity, etc.), or be inflatable, or made of a disposable material impregnated with pharmaceuticals, antimicrobials, etc. that is designed to come into direct contact with wounds.

Body portion 20 has a top edge 21, a bottom edge 22 and a pair of opposite side edges 23 and 24. Garment 10 also includes a plurality of bands 40. Each band 40 is releasably attachable onto flat body portion 20. As a result, each band 40 can be attached onto flat body portion 20 at a wide range of different locations. As will be shown, flat body portion 20 will be dimensioned to wrap around a patient's arm or leg while bands 40 wrap there around to apply a compression force to the body limb. Optionally, bands 40 may have loops 47 or pockets 48 to aid with donning.

As seen in FIGS. 1 and 2, top and bottom edges 21 and 22 may have measurement indicia thereon. Prior to use, the patient (or healthcare provider) will measure the circumference of the body limb at an upper end (e.g.: the calf, thigh or upper arm) and at the lower end (e.g.: the ankle or wrist or knee).

Next, portions of the side edges will be cut away such that the circumference of the top of the limb will correspond to the length of top edge 21 and the circumference of the bottom of the limb will correspond to the length of bottom edge 23. Specifically, these lengths would be somewhat smaller than the actual limb circumferences such that the bands provide the added length for complete coverage around the limb. For a limb with a larger upper circumference and smaller lower circumference, cutting away and removing these portions of the top edge will give the garment the axially tapered shape shown in FIG. 2. Preferably, body portion 20 will wrap at least half or three-quarters of the way around the body limb.

FIGS. 3A to 3C show three different shapes for body portion 20 (with a matching leg shown below). FIG. 3A shows a flat body portion 20 cut for a patient having a small calf and a small ankle. FIG. 3B is an illustration of the flat body portion dimensioned for a patient having a medium calf and a small ankle. Lastly, FIG. 3C is an illustration of the flat body portion dimensioned for a patient having a large calf and a small ankle. As can be seen, the present garment can be ideally contoured to the patient's leg (or arm) simply by cutting body portion 20 into a preferred shape. Moreover, this shape can be changed over time by progressively cutting away and removing more and more of the side portions. This is especially helpful when the patient's limb is getting smaller (as a result of the pressure being applied by the garment).

Figure 5:
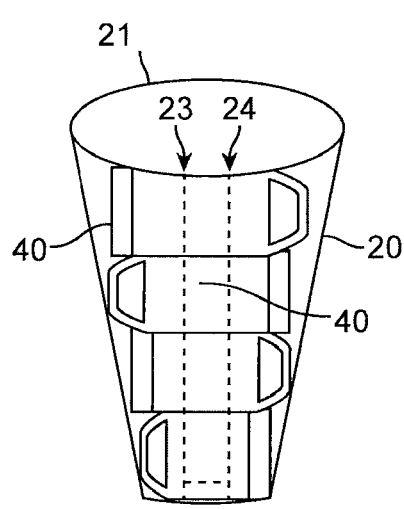
FIG. 5 is an illustration showing the wrapped garment with the bands in the closed position.

Next, as seen in FIG. 4, each of the bands 40 will be attached to body portion 20. In one optional preferred embodiment, bands 40 are simply attached onto flat body portion 20 by hook and loop (e.g.: Velcro®) fasteners, although other systems may be used as well. A band tensioning measurement card 41 can also be included. Card 41 has lines printed thereon at pre-set distances apart. Measurement indicia (i.e.: spaced apart lines 61) can be printed on bands 40. As each of bands 40 is stretched, their measurement indicia lines 61 move farther apart. The spacing of lines 61 on bands 40 can be compared to the spacing of the lines on card 41 such that pre-determined tensions can be set in the bands. Guides 43 can also be printed on body 20 to assist in the placement of bands 40. Finally, as shown in FIG. 5, the opposite edges 23 and 24 may be moved towards one another, partially wrapping around body portion 20 as shown. Thus, body portion 20 wraps most of the way around the limb and bands 40 also wrap partially around the limb. Typically, edges 23 and 24 will not contact one another as this would cause the garment to lose it's adjustability to a reduction in limb size. Instead, when the bands encompass a portion of the limb, it offers the benefit of being adjustable to changes in the limb size without having to re-cut and apply the bands to the new limb shape. Once the bands start to "bottom out", and the body portion completely covers the limb, it is then time to re-trim the body portion again to make the garment adjustable. As seen in the example of FIG. 5, bands 40 may be juxtaposed with each passing over opposite edges 23 and 24.

It is to be understood that the present invention provides two novel fitting systems to ensure that the garment is tailored to the individual. First, the size of body portion 20 can be cut to provide the optimal shape. Second, the position of bands 40 on body 20 can be varied.

Figure 6:
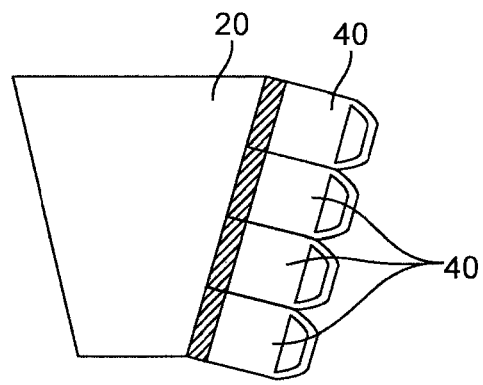
FIG. 6 is an embodiment showing all the bands extending from one side of the garment.
Figure 7A:
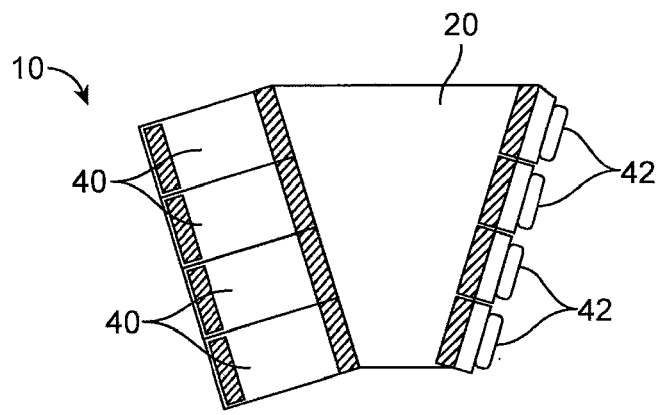
FIG. 7A is another embodiment showing all the bands extending from one side of the garment with D-rings mounted onto the other side of the garment.
Figure 7B:
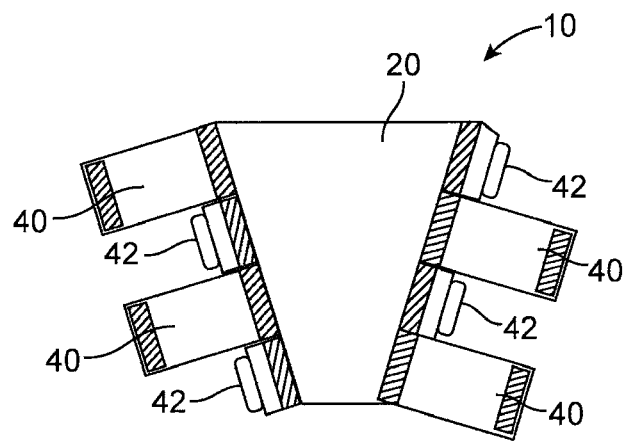
FIG. 7B is another embodiment with juxtaposed bands and corresponding D-rings mounted on opposite sides of the garment.

FIG. 6 illustrates an embodiment of the invention in which all of the bands 40 are attached to the same side of body 20. FIG. 7A illustrates another embodiment of the invention in which all of the bands 40 are again disposed on the same side of body 20. However, in this embodiment, each band 40 is passed through a corresponding (and preferably releasable) D-ring 42 and then looped back and fastened upon itself to wrap the garment around the body limb. The embodiment of FIG. 7B is similar to FIG. 7A except that the bands 40 (with their corresponding D-rings 42) now extend from opposite sides such that the bands are juxtaposed with respect to one another.

Figure 8A:
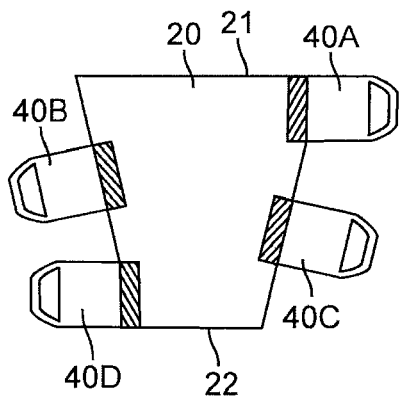
FIG. 8A is an illustration of an alternate position of the bands attached to the body portion.
Figure 8B:
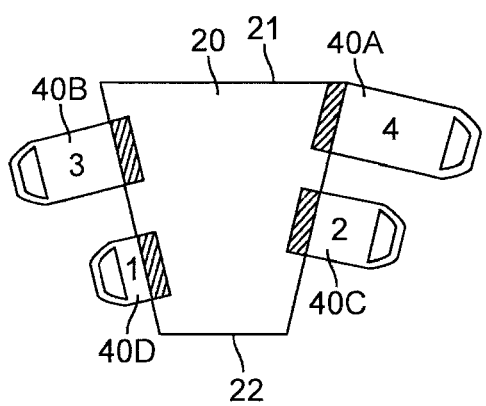
FIG. 8B is an embodiment with bands of different lengths.
Figure 8C:
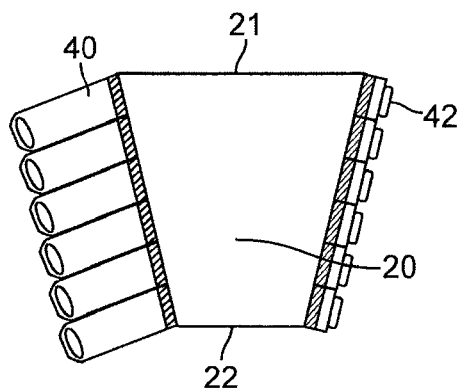
FIG. 8C is an embodiment with six bands.

FIG. 8 shows one example of alternate placement locations of bands 40 on body portion 20. Specifically, bands 40A and 40D are positioned parallel to edges 21 and 22; whereas bands 40B and 40C are positioned at different angles with respect to top and bottom edges 21 and 22, at an angle perpendicular to the body contour. It is to be understood that the band positions shown in FIG. 8A are merely exemplary and that limitless possibilities exist for locations to attach bands 40 to body 20. As seen in FIG. 8B, each of bands 40 may be of different lengths. FIG. 8C shows an embodiment with six bands instead of four. It is to be understood that the total number and lengths of bands 40 can be varied, all keeping within the scope of the present invention.

Figure 9:
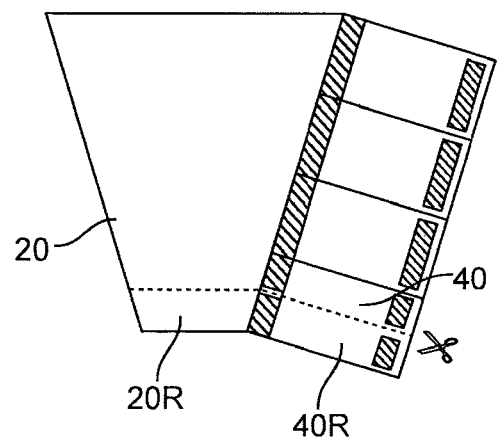
FIG. 9 is an illustration showing a bottom cut away portion of the garment.

FIG. 9 illustrates trimming of the garment prior to use. Specifically, a cut away portion 20R is removed from body 20 as a cut away portion 40R is removed from band 40. Removal of portions 20R and 40R results in a garment having a shorter axial length. Alternatively, the cut away portion 20R could instead be at the top of the garment.

Figure 10A:
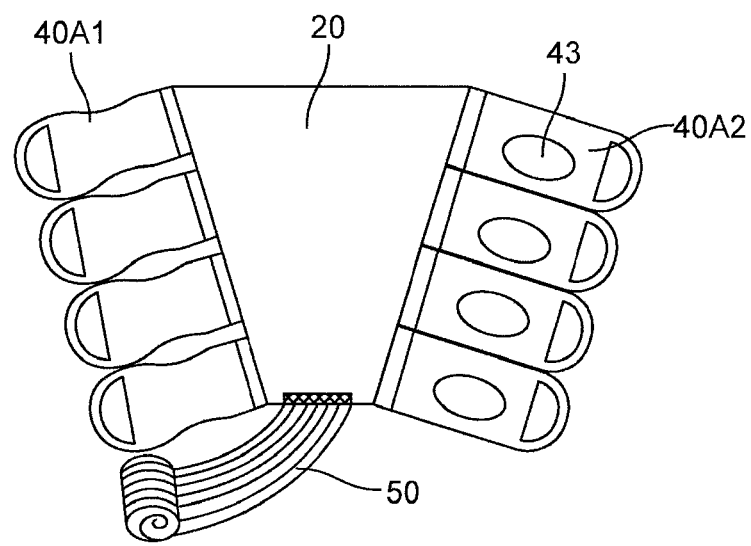
FIG. 10A is an embodiment of the invention having interlocking bands and an attached foot wrap.
Figure 10B:
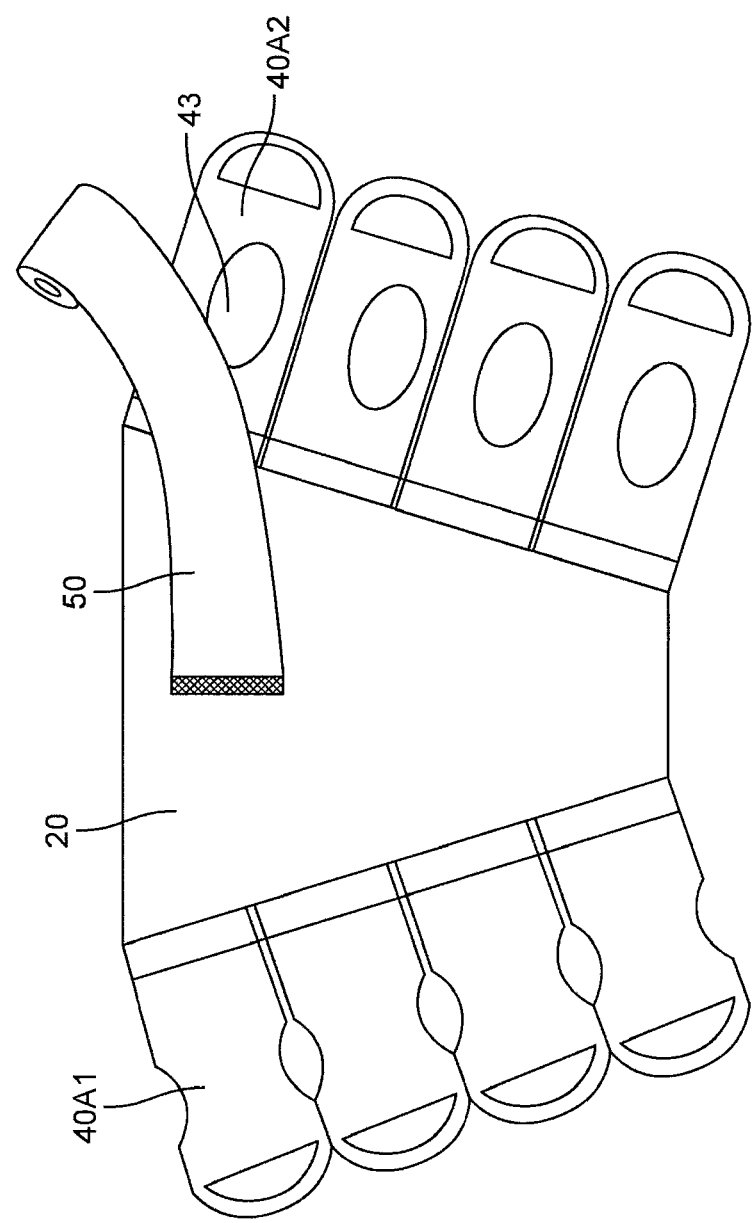
FIG. 10B is similar to FIG. 10A, but the wrap extends from an alternate location.
Figure 10E:
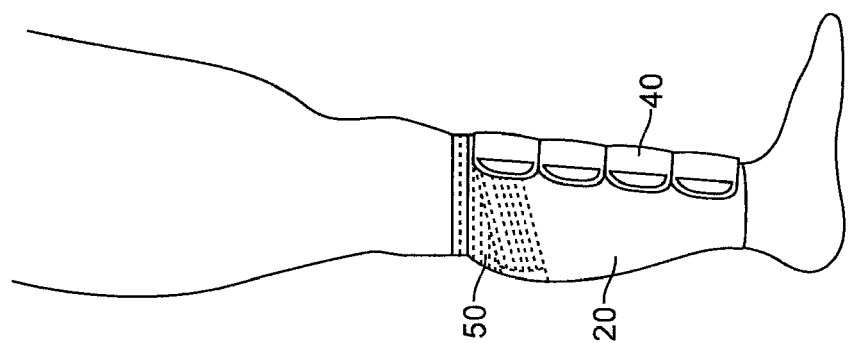
FIG. 10C to 10E show three alternate placement locations for the wrap.
Figure 10D:
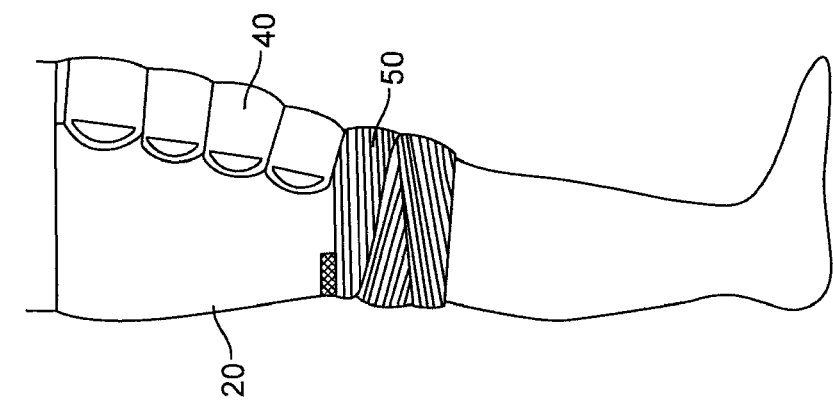
Figure 10C:
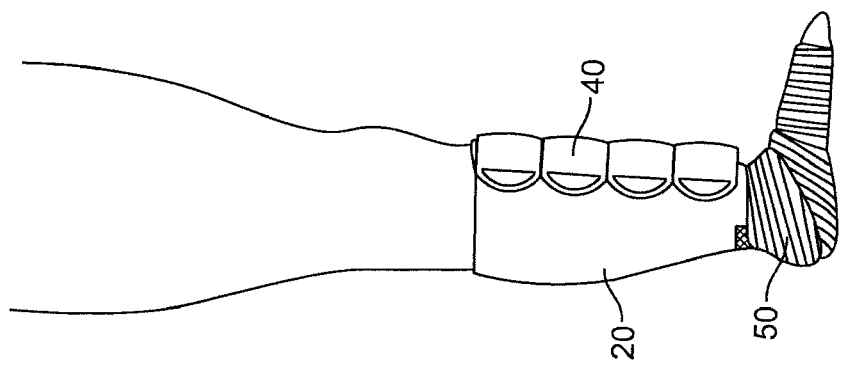

FIG. 10A illustrates an embodiment of the invention having interlocking bands. Specifically, the end of band 40A1 is passed through hole 43 in corresponding band 40A2. Thereafter, Velcro® patches on either or both of the ends of bands 40A1 and 40A2 may be used to fasten these ends together. An optional attached foot or knee wrap 50 is also included. Wrap 50 may also be a non-slip band applied to the bottom (or top) edge of body 20 to keep the garment in place. As seen in FIG. 10B, wrap 50 may be placed at alternate locations on body 20. For example, as seen in FIG. 10C, wrap 50 may be wrapped around the ankle. As seen in FIG. 10D, wrap 50 may be wrapped around the knee. Or as seen in FIG. 10E, wrap 50 may be wrapped just below the knee.

Figure 11:
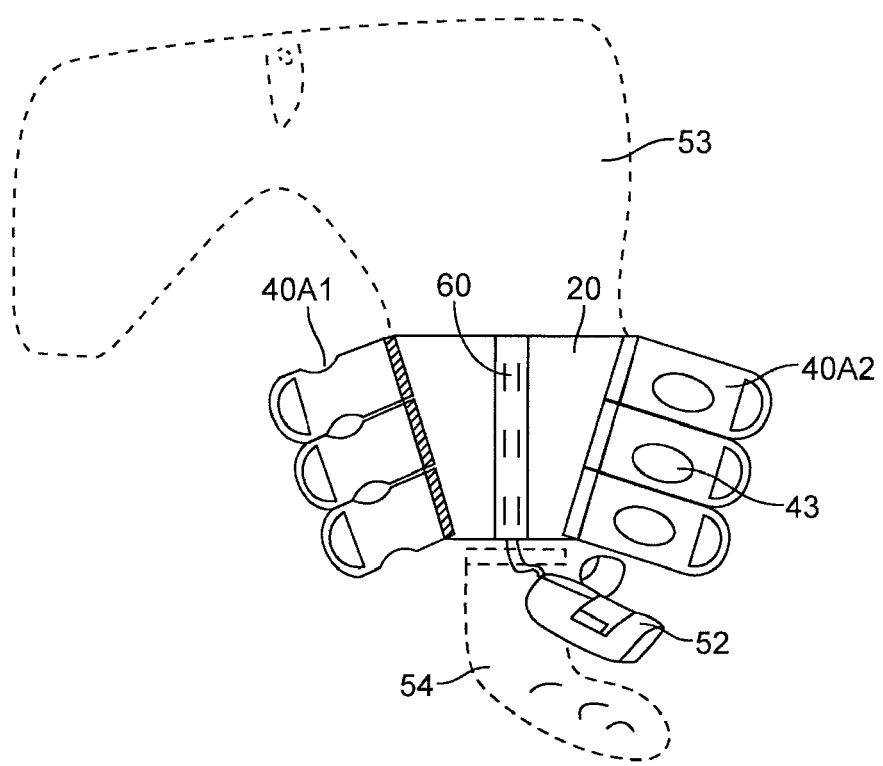
FIG. 11 is an embodiment of the invention having interlocking bands, a compression measuring system and an ankle-foot wrap.

FIG. 11 illustrates an embodiment similar to FIG. 10, but now includes a measurement system 60. Preferably, system 60 comprises lines 61 printed on body portion 20. As body portion 20 is stretched, pairs of lines 61 move apart from one another. The spacing between each of the pairs of lines 61 thus corresponds to the tension in body 20 at that location. An advantage of this system is that fewer tension measurements can be made than the number of bands. For example, the system may use six bands, but only three pairs of lines 61. Thus, only three tension measurements need to be made to fit the garment. Optionally, the present invention also includes a "Built-In Pressure System™" and guide card. The patient's ankle circumference measurement determines the appropriate range on the Built-In Pressure System card for the patient. This eliminates the need to translate the patient's ankle circumference into a nominal size, furthermore simplifying the fitting process. The Built-in Pressure System card allows the patient to adjust the garment to the prescribed amount of compression. An optional an ankle/foot wrap 52 is also included. Additionally, optional compression pants 53 or a compression anklet 54 (shown in dotted lines) may also be attached.

Figure 12A:
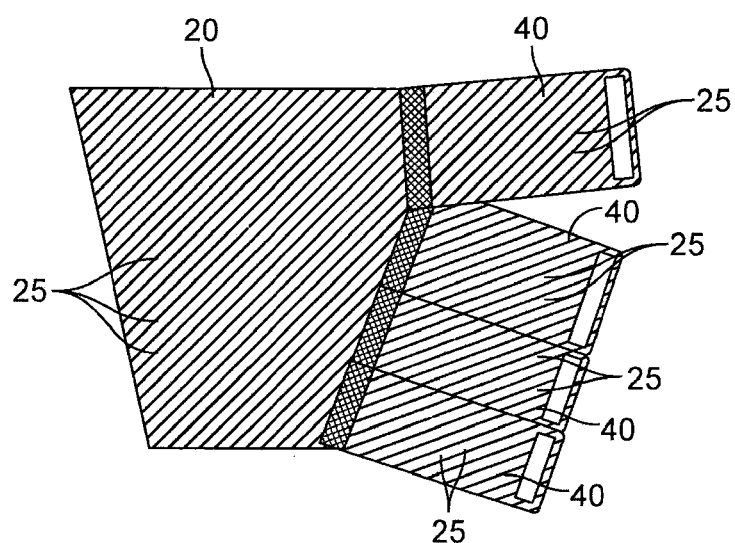
FIG. 12A is an embodiment of the invention having flow channels in the body portion also showing alternate angling of a top band for improved contouring.

FIG. 12A illustrates an embodiment in which the inner (i.e.: limb facing) surface of flat body portion 20 has directional seams which narrow the thickness of the flat body portion such that the alternating channels 25 of high and low pressure are created running along the body limb. FIG. 12B is a corresponding side profile view. Moreover, it is to be understood that seams are not required to make the present channels. For example, foams and laminates can be channeled without seams. Moreover, bands 40 may also have channels 25. Channels 25 on either or both of body portion 20 and bands 40 may vary in angle and spacing as desired.

FIG. 13 illustrates an embodiment in which each of bands 40 have reinforcement tabs 45 securing them to flat body portion 20. Reinforcement tabs 45 may simply be hook or loop fasteners having greater strength than the hook or loop fasteners found at the ends of bands 40. Thus, pulling on bands 40 will cause the bands to release from the opposite side of the garment (instead of simply being pulled off the garment completely). Thus, pulling on the bands to tighten, adjust, or remove the garment will not cause bands 40 to come off the body portion 20.

FIGS. 14A to 14C show the sequence of positioning all of the bands on one side of the body portion (FIG. 14A), and then wrapping the garment around a body limb (FIG. 14B) followed by opening the garment after the fitting is done (FIG. 14C). Excess material 20R can also be trimmed after initial fitting.

FIG. 15 illustrates the interior (patient limb facing) side of body portion 20. A strip 26 is provided for attachment of an additional foam pad 28A. Strip 26 is made of a hook and loop compatible material. Alternatively, a wound dressing 28B may be attached to body 20 (for treating skin that requires a primary dressing before applying the compressive layer).

Figure 16A:
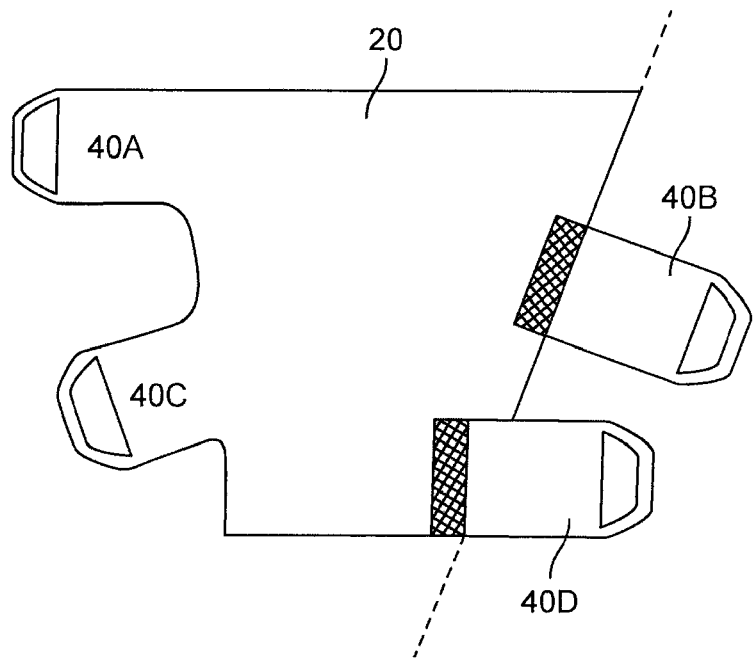
FIG. 16A is an embodiment of the invention with two positional bands and two fixed bands.
Figure 16B:
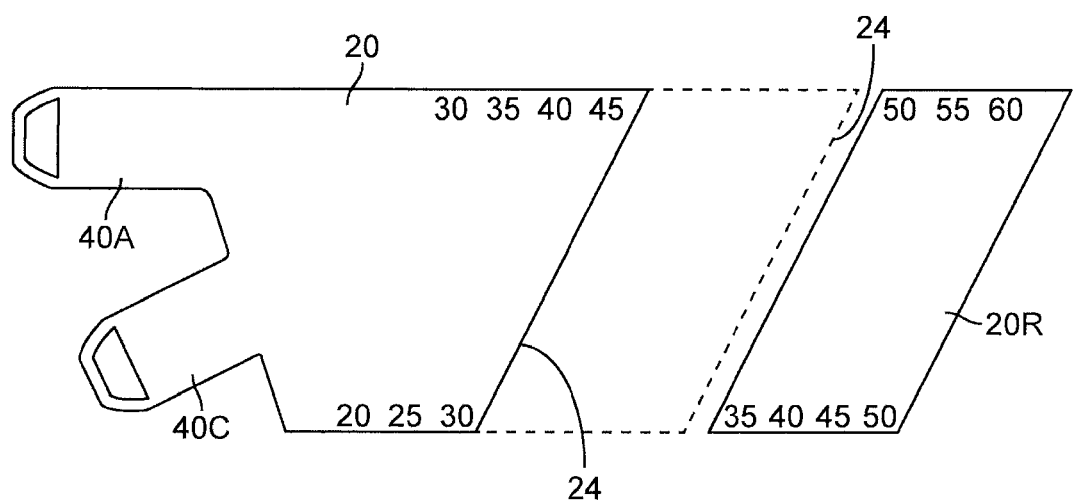
FIG. 16B shows the cutting of the body portion of FIG. 16A.
Figure 16C:
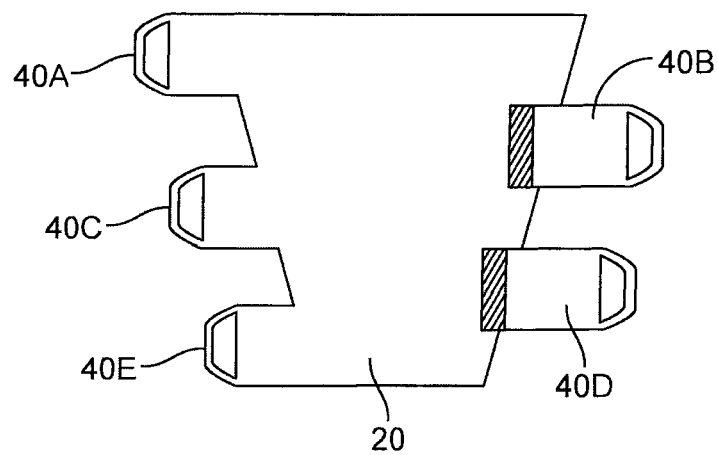
FIG. 16C shows the positioning of the bands on a body portion.
Figure 16D:
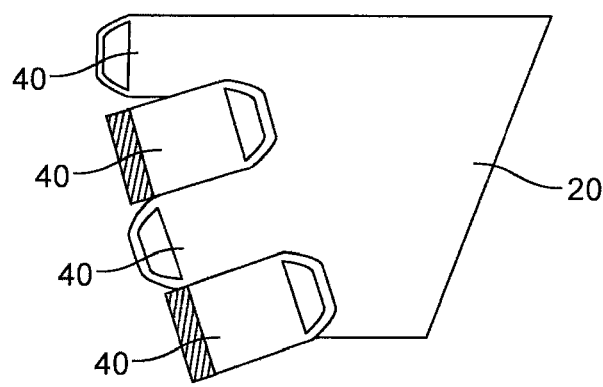
FIG. 16D shows an alternate positioning of the bands.
Figure 16E:
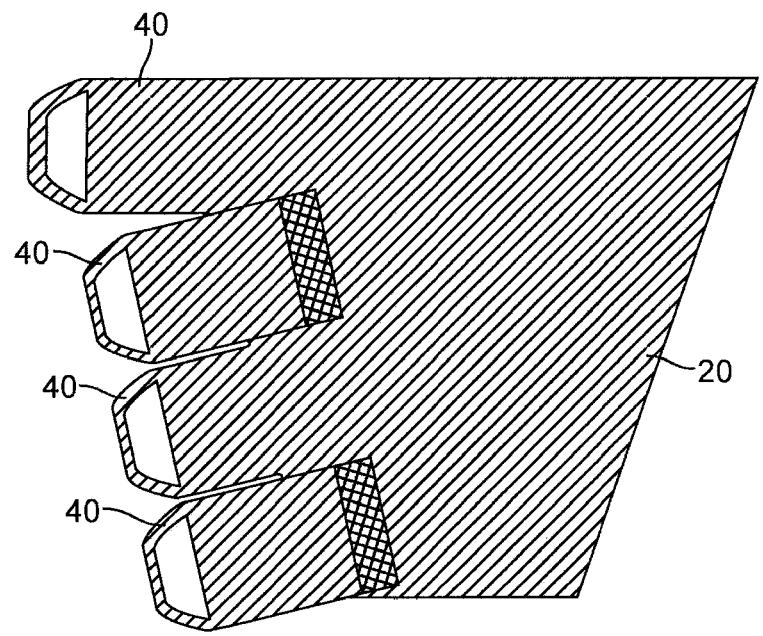
FIG. 16E shows an alternate positioning of the bands.
Figure 16F:
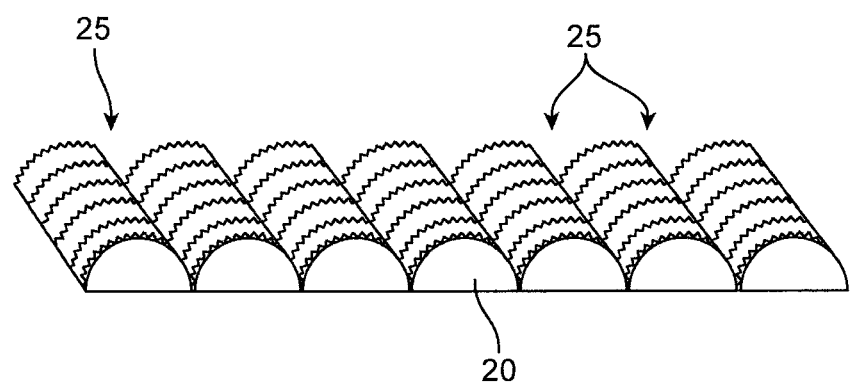
FIG. 16F shows a perspective view of high and low pressure channels in the garment.

FIGS. 16A, 16B, 16D and 16E show an alternate embodiment of the invention having two bands 40A and 40C that are an integral part of body 20 and two bands 40B and 40D that are separate from body 20. In FIG. 16B, the user first cuts away a portion of side 24, removing portion 20R. Next, bands 40B and 40D are attached as shown in FIG. 16A. Alternatively, as seen in FIG. 16C, body portion 20 may instead have three integral bands 40A, 40C and 40E. Other numbers of bands 40 (including a single band) are all encompassed within the present invention. Alternatively, as shown in FIG. 16D, bands 40 can be pre-applied before fitting. Once the garment is wrapped around the body portion, the band ends can be released such that the bands are configured as shown in FIGS. 14A to 14C. Or, as shown in FIG. 16E, bands 40 can all extend from the same side of body portion 20 when initially being applied. FIG. 16F shows a perspective view of the high and low pressure channels 25 in the garment.

FIGS. 17A and 17B show a one piece body 20 that is wrapped onto itself. In operation, cylindrical body 20 is slid onto the body limb and then folded over on top of itself (FIG. 17A). Next, bands 40 are attached over the fold in body 20 (FIG. 17B). Optionally, the cylindrical body 20 may be cut along the folds. The advantage of this approach is that the garment sizes itself to the limb without the need for measuring or indicia.

The present invention also provides a method of fitting a compression garment to a body limb, comprising: assembling a compression garment around the body limb, wherein the compression garment comprises a body portion 20 and a plurality of bands 40, by: (i) selecting a position at which each of the plurality of bands 40 are to be attached to body portion 20; (ii) attaching each of the plurality of bands 40 to body portion 20; (iii) wrapping body portion 20 around a body limb; and then (iv) wrapping each of the plurality of bands 40 around part of body portion 20 to apply a therapeutic compression to the body limb.

The preferred method may also comprise: (v) cutting the body portion to a preferred size prior to attaching the plurality of bands to the body portion, by: (i) measuring the circumference of a body portion at two or more locations, and (ii) tapering the flat body portion such that the top and bottom edges of the flat body portion correspond to the circumference of the body limb at each of the two locations. The dimensions where the body limb circumference may be measured may be (i) calf and ankle circumferences, or (ii) upper arm and wrist circumferences. In addition, by determining the body portion circumference location at more than two locations, a more defined body contour can be achieved. It is to be understood, however, that the present invention also encompasses taking only one body circumference fitting measurement.

Wrapping bands 40 around part of the body portion 20 may comprise: (i) pulling together the opposite side edges of the body portion, and (ii) wrapping the bands across the opposite side edges of the body portion.

Advantageously, in accordance with the preferred method, the size of body portion 20 may be changed during fitting while the size of bands 40 are not changed during fitting.

FIGS. 18A to 18D show various optional embodiments of the invention having a bridge portion 20B positioned between portions 20. Bridge portion 20B could be used to extend the circumference of the garment if the limb diameter increases. Optionally, a series of multiple bridge portions 20B could also be used to eliminate trimming waste since instead of trimming down, multiple bridges could be added to build up to the required fit. Alternatively, bridge portion 20B could be made of a different material than the remainder of body portion 20. For example, bridge portion 20B could be made of a stiffer material to make the garment stay in place or to act as an orthotic, or a guide sock or compression socking 54 could also act as a bridge as shown in 18B. Moreover, bridge portion 20B could instead be made of a more elastic material, or the user could be supplied with a series of bridges 20B, each with a different stiffness. These different stiffness levels can preferable each relate to a known compression level when applied with just enough tension to reach maximum elongation.

Figure 19A:
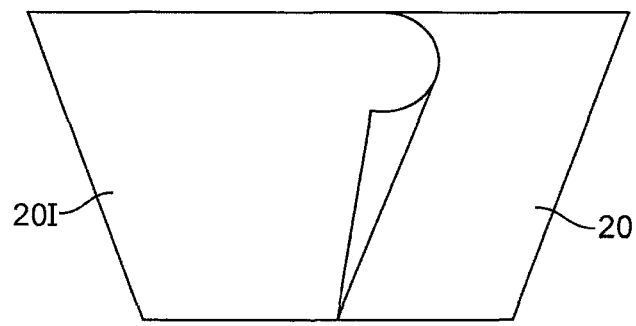
FIGS. 19A and 19B show materials attached to the body portion to vary the stiffness of the garment.
Figure 19B:
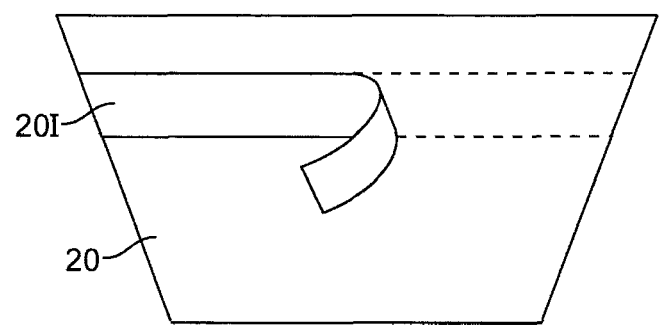
Figure 19C:
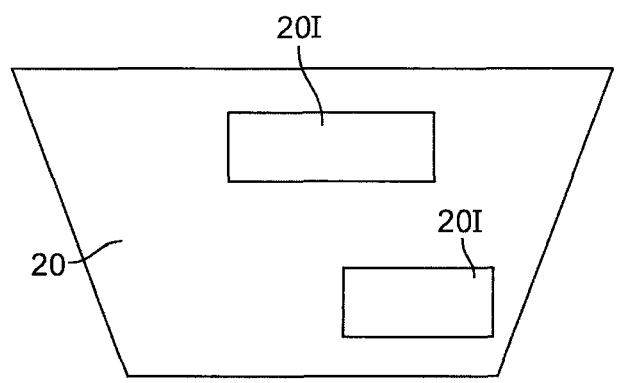
FIG. 19C shows an embodiment having an inelastic material attached to the body portion of the garment.

FIGS. 19A to 19C show embodiments where materials are attached to the body portion 20 to vary its stiffness. In FIG. 19A, material 201 covers body portion 20 and varies its stiffness. In FIG. 19B, a strip of material 201 is placed onto body 20 to vary its stiffness in this local region. In FIG. 19C, a pair of material strips 201 vary the stiffness in the regions where they are applied. In preferred embodiments, material 201 may be inelastic. For example, in FIG. 19B, an inelastic material 201 may optionally be positioned adjacent to the patient's calf to reinforce the calf muscle action pumping fluid out of the leg.

Figure 20:
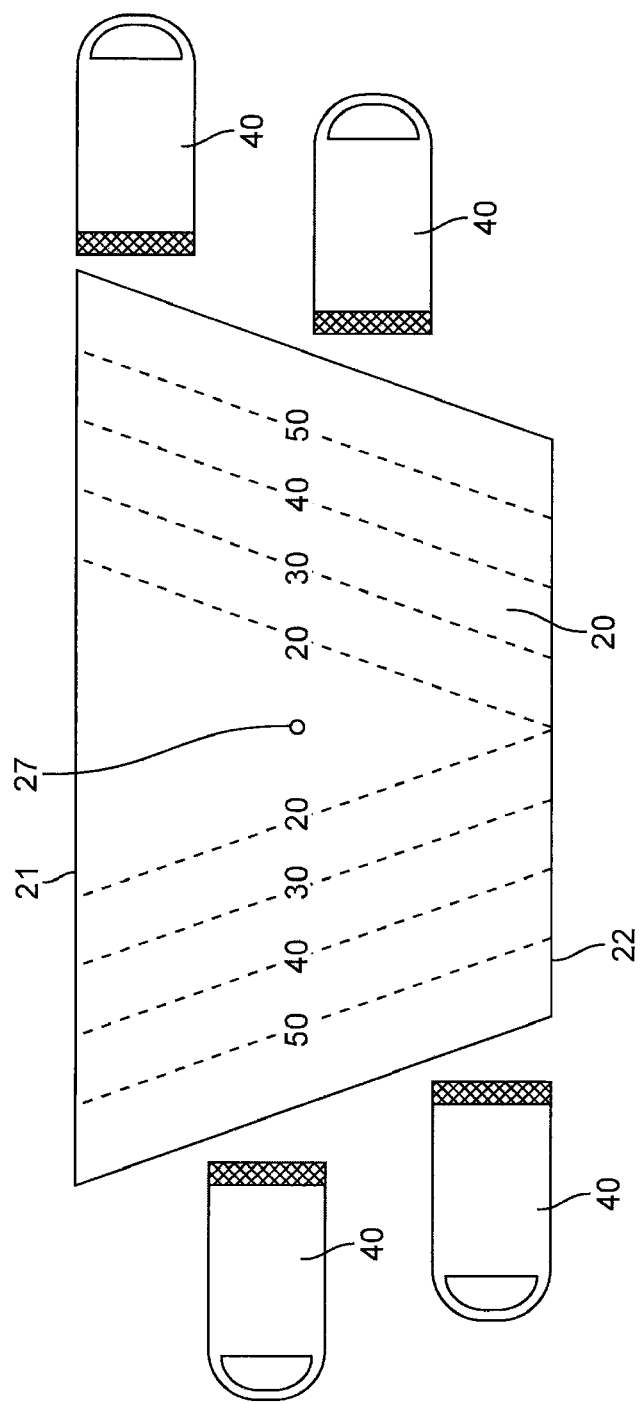
FIG. 20 is an embodiment of the invention in which fitting measurements are only taken at the mid-point of the body.

FIG. 20 is an embodiment of the invention in which fitting indicia (i.e.: the dotted lines marked 20, 30 and 40) extend the full top to bottom distance of the device. In this embodiment, it is only necessary to take fitting measurements at mid-point 27 (i.e.: measure the separation distances between dotted lines 20-20, or 30-30 etc. from mid-point 27). Advantageously, all other fitting measurements are assumed.

Figure 21:
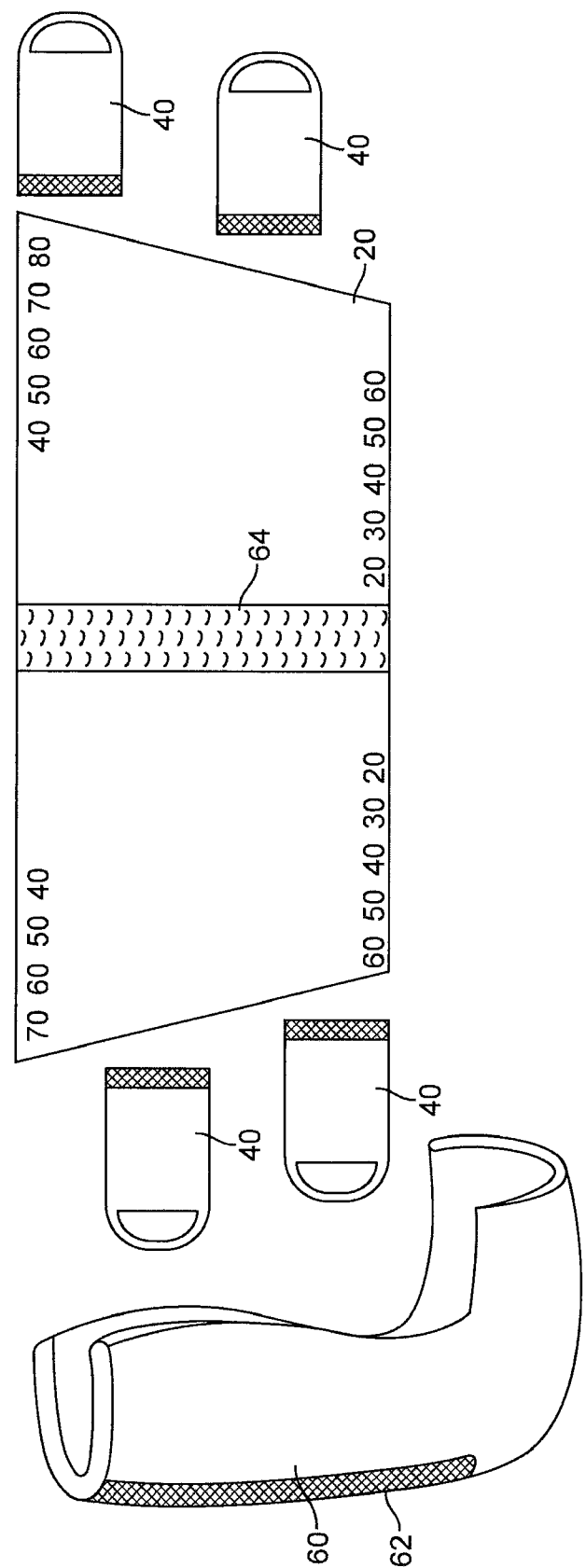
FIG. 21 is an embodiment supporting and wrapping around an orthotic insert.

FIG. 21 is an embodiment of the invention that wraps around an orthotic insert. Specifically, a leg orthotic support 60 and body portion 20 can be provided with respective hook and loop fasteners 62 and 64. In operation, orthotic support 60 is fastened onto body portion 20, and body portion 20 and its associated bands 40 are than wrapped around the limb. An orthotic insert that is jointed may also be used as desired. It is to be understood that the present invention can be used to hold other devices in place, not just wound dressings and orthotics.

Figure 22A:
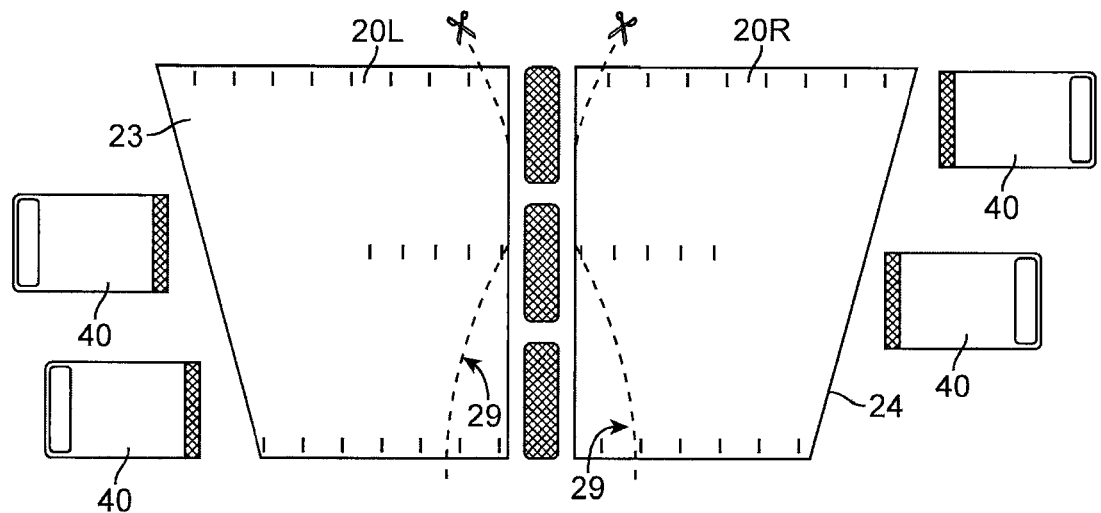
FIGS. 22A and 22B are a first example of a three dimensional garment.
Figure 22B:
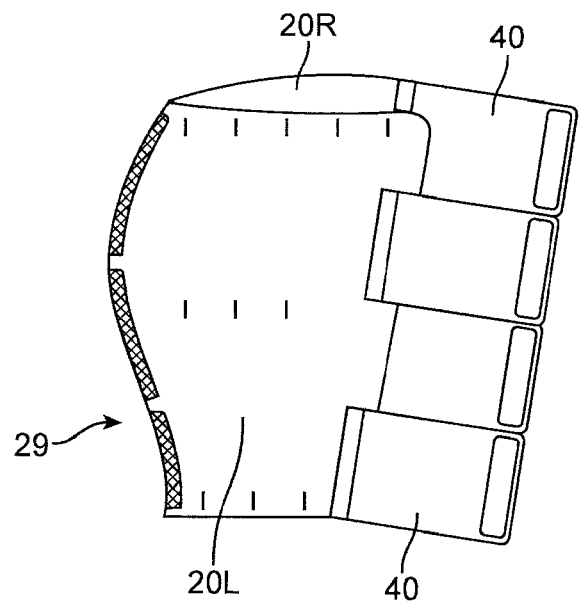

FIGS. 22A and 22B illustrate the flat (FIG. 22A) and assembled (FIG. 22B) views of a three dimensional garment that contours to the body limb. In FIG. 22A, body portion 20 made from a left portion 20L and a right portion 20R. Portions 20L and 20R each have indented areas 29. As seen in FIG. 22B, when portions 20L and 20R are attached together (e.g.: by hook and loop fasteners), the garment will have a shape that better contours to the leg. Bands 40 are than attached thereto, similar to the embodiments described above. It is to be understood that one or more bridge portions as described herein may also be used with this embodiment of the invention.

Figure 23B:
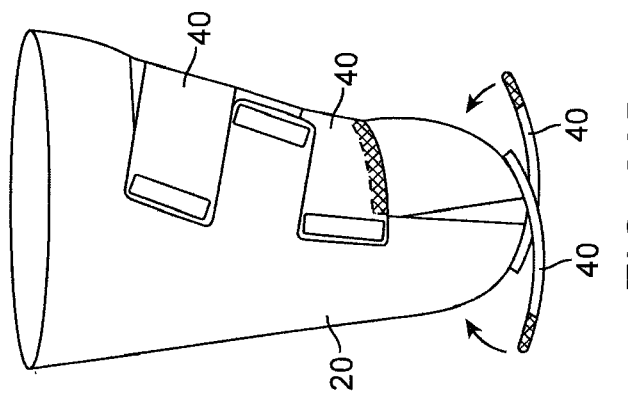
FIGS. 23A and 23B are a second example of a three dimensional garment.
Figure 23A:
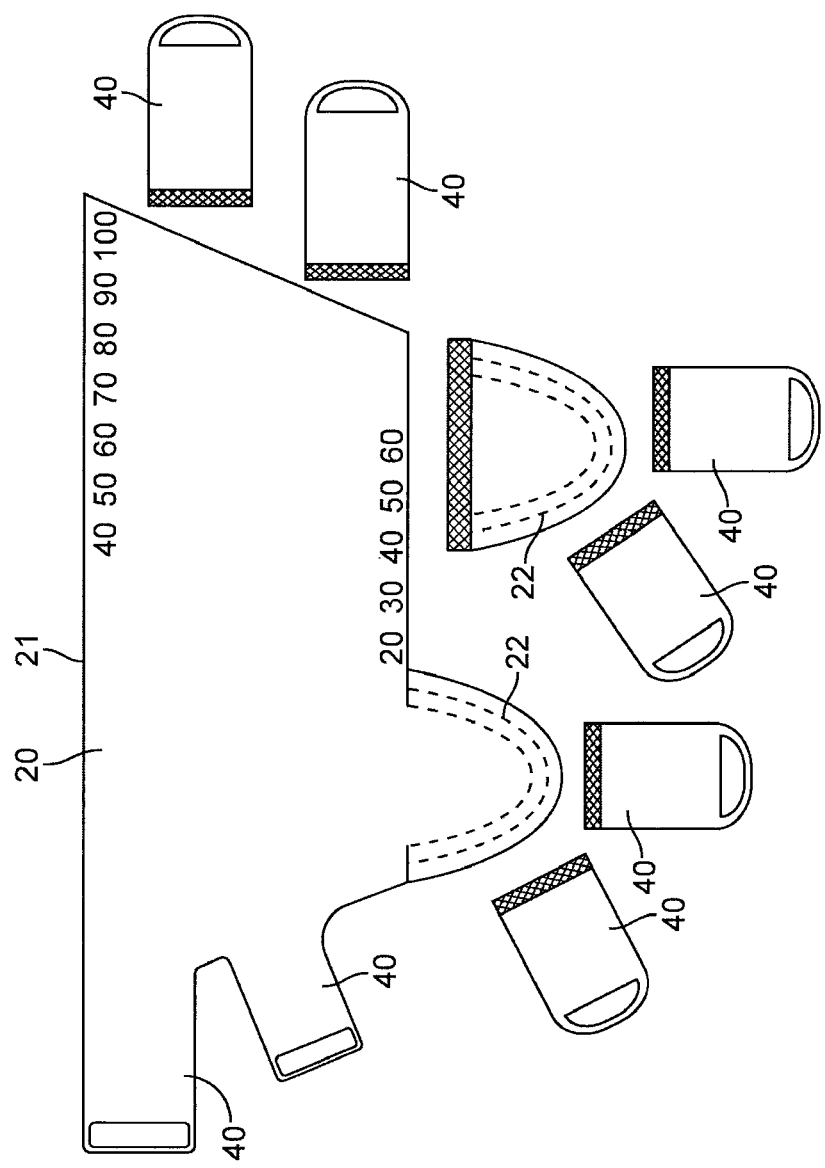

FIGS. 23A and 23B illustrate the flat (FIG. 23A) and assembled (FIG. 23B) views of a three dimensional garment that contours to a patient's leg. In FIG. 23A, a novel shaped body portion 20 is provided together with a plurality of bands 40. As seen in FIG. 23B, when bottom edge 22 is wrapped together, it will form a cup in which to support the patient's leg. Bands 40 are then attached thereto (or extend therefrom), similar to the embodiments described above. The dotted line portions along bottom edge 22 can be cut away to better adjust the shape the to particular patient's leg/foot. Moreover, as can be seen, the portions forming bottom edge 22 can either be integral to body 20 or attached thereto. These cupped portions are beneficial for providing compression to the heel or an amputated limb stump.

Figure 24A:
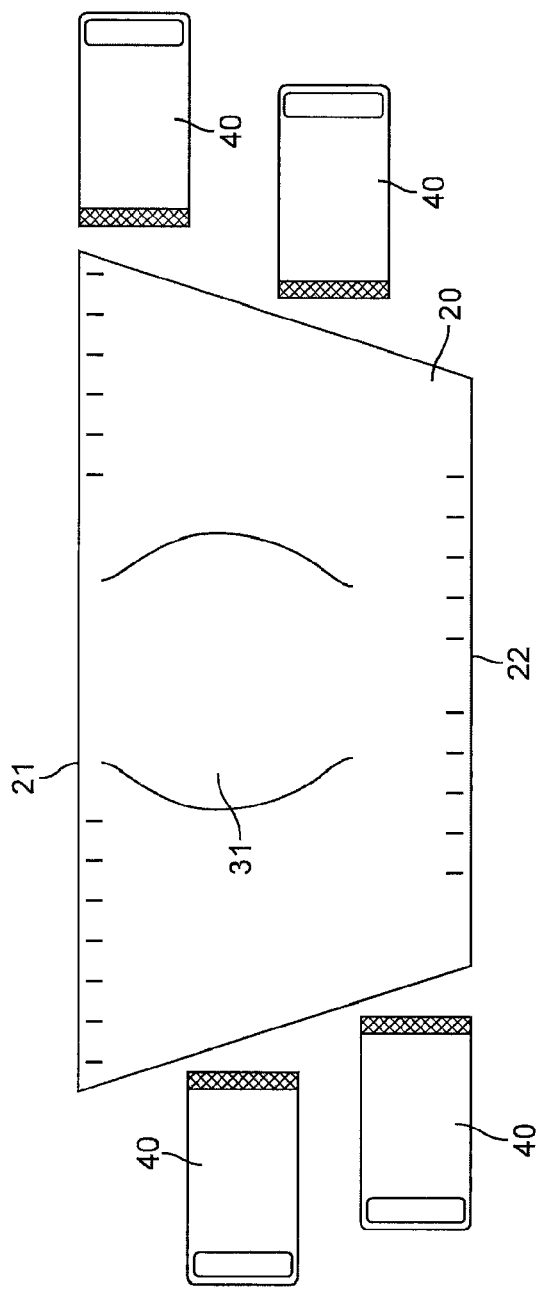
FIGS. 24A and 24B are a third example of a three dimensional garment.
Figure 24B:
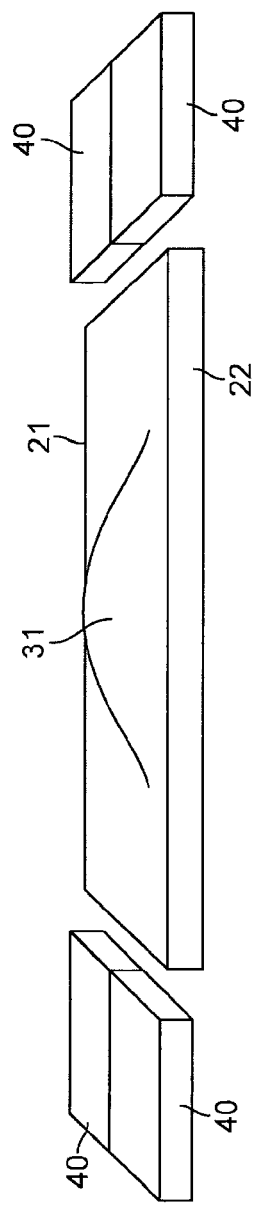

FIGS. 24A and 24B show flat (FIG. 24A) and angled perspective (FIG. 24B) views of a garment having a preformed indentation 31 therein. The three dimensional shaping provided by indentation 31 can assist in shaping the device to a patient's leg. Alternatively, the space provided under indentation 31 could be used for placing bandages or dressings.

Figure 25:
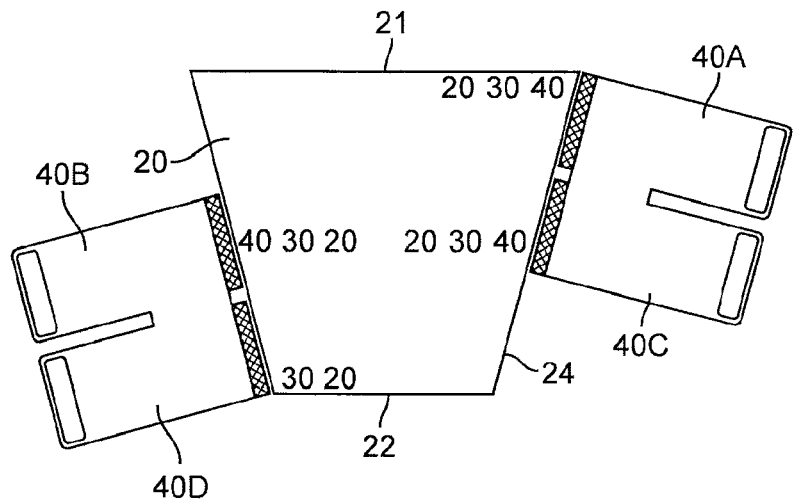
FIG. 25 is an embodiment of the garment in which bands are attached to the body portion in pairs or sets.

FIG. 25 shows an embodiment of the invention in which bands are attached onto the body portion in sets. Specifically, bands 40A and 40C are provided on the same pad of material that is attached to body 20. Similarly, bands 40B and 40D are provided on another pad of material that is attached to body 20. It is to be understood that bands 40 may be attached in sets of two or three or any other number.

Figure 26:
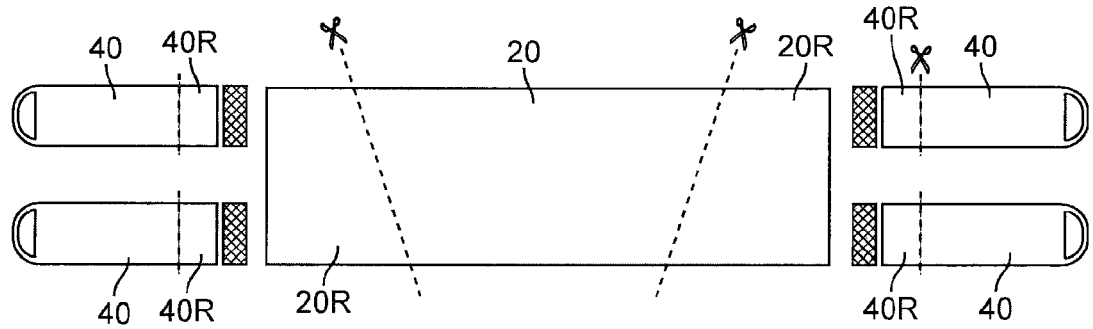
FIG. 26 is an embodiment showing removable body and band portions.

FIG. 26 is an embodiment showing removable body and band portions.

Figure 27:
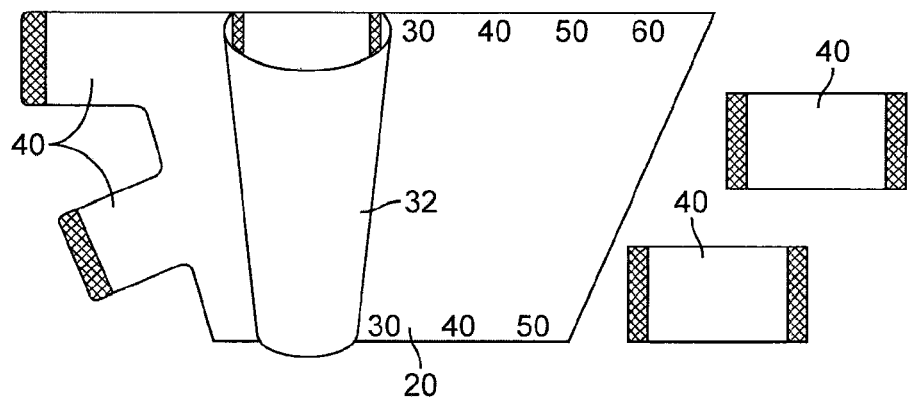
FIG. 27 is an embodiment showing an internal guide sleeve.

Lastly, FIG. 27 is an embodiment showing an internal guide sleeve 32 to protect the patient's skin from band edges, etc. Internal guide sleeve 27 can help keep the garment in place, aid in donning the garment, or be padded for added comfort or even be inflatable to change pressure, as desired. Moreover, internal guide sleeve 27 can optionally be impregnated with pharmaceuticals, etc.

What is claimed is:

1. A garment, comprising:
a body portion dimensioned to be wrapped around a part of a patient's limb, the body portion comprising a top edge, a bottom edge and a pair of opposite side edges, wherein the body portion is trimmable between the edges permitting the body portion to correspond to any shape of the part of the patient's limb, and
wherein one or more cut away portions on the edges can be removed so that a width of a top edge of the body portion corresponds to a top circumference of the limb and a width of a bottom edge of the body portion corresponds to a bottom circumference of the limb; and
a plurality of bands, wherein each band is removably positionable onto the body portion at a plurality of different orientations relative to any of the edges,
wherein a proximal edge of each band is removably attached onto the body portion and a distal edge of each band extends away from the proximal edge, and
wherein the distal edge of each band wraps around a part of the body portion when the body portion is wrapped around the part of the patient's limb to apply a compression force to the patient's limb.

2. The garment of claim 1, wherein the body portion wraps around a portion of the top and bottom circumferences of the limb.

3. The garment of claim 1, wherein the body portion wraps around more than three quarters of the top and bottom circumference of the limb.

4. The garment of claim 1, wherein a top edge of the body portion is wider than a bottom edge, and wherein opposite side edges of the body portion taper inwardly from the top to bottom edges.

5. The garment of claim 1, wherein the plurality of bands are positionable onto the body portion by hook and loop fasteners.

6. The garment of claim 1, wherein the plurality of bands are positionable onto the body portion using D-rings.

7. The garment of claim 1, wherein the body portion comprises alternating channels of high and low pressure.

8. The garment of claim 1, wherein one or more bands of the plurality of bands extending from a first side edge of the body portion are juxtaposed between bands extending from an opposing second side edge of the body portion.

9. The garment of claim 1, wherein the body portion has trimmable regions for shortening a length of the garment along the limb.

10. The garment of claim 9, wherein the one or more of the plurality of bands extend from different opposing side edges of the body portion.

11. The garment of claim 1, wherein one or more of the plurality of bands comprise trimmable portions to shorten their respective length.

12. The garment of claim 1, wherein one or more of the plurality of bands extend from a same side edge of the body portion.

13. The garment of claim 1, further comprising a wrap attached to a bottom edge of the body portion to apply compression adjacent to the garment.

14. The garment of claim 1, further comprising reinforcement tabs securing the proximal or distal edges of each band onto the body portion.

15. The garment of claim 1, wherein one end of each band adheres more strongly to the body portion than the other end.

16. The garment of claim 1, wherein the plurality of bands are positionable to the body portion in sets or pairs.

17. The garment of claim 1, wherein the body portion comprises a bridge portion.

18. The garment of claim 17 wherein the bridge portion has a different stretchability than the remainder of the body portion.

19. The garment of claim 1, further comprising an orthotic insert wrapped within the body portion or a wound dressing attached to the body portion.

20. The garment of claim 1, wherein the body portion comprises measurement indicia, and wherein the measurement indicia corresponds to a respective circumference of the limb such that one or more trimmable portions on edges of the body portion can be removed so that a width of a top edge of the body portion corresponds to a top circumference of the limb and a width of a bottom edge of the body portion corresponds to a bottom circumference of the limb.

\* \* \* \* \*